United States Patent
Fox et al.

(10) Patent No.: US 12,016,284 B2
(45) Date of Patent: Jun. 25, 2024

(54) BARLEY CULTIVAR AS-WOLF

(71) Applicants: Gregory Joseph Fox, West Fargo, ND (US); Christine Elizabeth Fastnaught, West Fargo, ND (US); Steven Murray Fox, West Fargo, ND (US)

(72) Inventors: Gregory Joseph Fox, West Fargo, ND (US); Christine Elizabeth Fastnaught, West Fargo, ND (US); Steven Murray Fox, West Fargo, ND (US)

(73) Assignee: 21st Century Genetics Corp., West Fargo, ND (US)

( * ) Notice: Subject to any disclaimer, the term of this patent is extended or adjusted under 35 U.S.C. 154(b) by 203 days.

(21) Appl. No.: 17/681,602

(22) Filed: Feb. 25, 2022

(65) Prior Publication Data
US 2022/0272925 A1  Sep. 1, 2022

Related U.S. Application Data

(60) Provisional application No. 63/154,036, filed on Feb. 26, 2021.

(51) Int. Cl.
*A01H 6/46* (2018.01)
*A01H 5/10* (2018.01)

(52) U.S. Cl.
CPC ............. *A01H 6/4624* (2018.05); *A01H 5/10* (2013.01)

(58) Field of Classification Search
CPC .................................................. A01H 6/4624
See application file for complete search history.

(56) References Cited

U.S. PATENT DOCUMENTS 10,653,086 B1 *  5/2020  Fastnaught .......... A01H 6/4624

OTHER PUBLICATIONS

Association of Official Seed Certifying Agencies, a Report of the Small Grain Variety Review Board, Mar. 24, 2020, p. 45, Moline, IL. aosca.org/wp-content/uploads/2020/06/2020SGJAN_Report_FINAL.pdf.
Association of Official Seed Certifying Agencies, a Report of the Small Grain Variety Review Board, Aug. 17, 2021, p. 8, Moline, IL. aosca.org/wp-content/uploads/2022/02/2021SGJUL_Report_FINAL.pdf.

* cited by examiner

*Primary Examiner* — David H Kruse

(57) ABSTRACT

A barley variety designated AS-Wolf, the plants, seeds and plant parts of barley variety AS-Wolf, methods for producing a barley plant produced by crossing the variety AS-Wolf with itself or another barley plant, and hybrid barley seeds and plants produced by crossing the variety AS-Wolf with another barley line or plant, and the creation of variants of variety AS-Wolf by backcrossing, mutagenesis, haploid systems, cell and tissue culture or transformation utilizing transgenes are disclosed. Methods for producing other barley varieties or breeding lines derived from barley variety AS-Wolf and to barley varieties or breeding lines produced by those methods are also provided. Barley variety AS-Wolf demonstrates a unique combination of traits for the human food market including waxy starch, hulless seed and increased levels of beta-glucan fiber.

19 Claims, No Drawings

BARLEY CULTIVAR AS-WOLF

This application claims the benefit of U.S. Provisional Appl. Ser. No. 63/154,036 filed Feb. 26, 2021, the entire disclosure of which is incorporated herein by reference.

FIELD OF INVENTION

This invention relates to the field of barley (*Hordeum vulgare* L.) breeding, specifically to a new and distinctive barley cultivar designated AS-Wolf.

BACKGROUND OF INVENTION

There are numerous steps in the development of a novel, desirable plant germplasm through plant breeding. Plant breeding can begin with the analysis and definition of problems and weaknesses of the current germplasm (e.g., seeds or plant tissue), the establishment of breeding goals, and the establishment of breeding objectives. Then, a germplasm that possess the traits to meet the breeding goals can be selected. The purpose of such plant breeding can be to create an improved combination of desirable traits from multiple parental germplasms in a single variety.

Barley (*Hordeum vulgare* L.), a type of plant than can be bred, is an important and valuable field crop. Barley breeders seek to develop stable, high yielding barley varieties that are agronomically sound and have good grain quality for its intended use. Barley varieties may differ from each other in one or more traits and can be classified and differentiated according to the specific traits they possess. For example, barley can be two-rowed or six-rowed, which refers to the number and positioning of kernels on the spike (otherwise known as the head). Barley can also be classified as spring barley or winter barley, referring to the growth habit, or by the adherence of hulls on the seed, or by the type of starch in the seed. Additionally, barley varieties can be differentiated based on grain yield, beta-glucan content, lodging, heading date, plant height, awn length, and whether the endosperm is shrunken or plump. Additional traits may also differentiate various barley lines.

Barley is a grain that is grown worldwide with three main market classes, malt, feed and food. Most of the barley grain produced in the United States is used as an ingredient in cattle, pig, or poultry feed. Another major use for barley is malt production. Malt is used in the brewing and distilling industries to produce alcoholic beverages. Barley varieties that are preferred for producing malt are selected on the basis of characteristics such as kernel plumpness, low protein content and low Beta-glucan content. Significant overlap between the classes can occur since barley that does not meet malting specifications can be used for feed, food and potentially the emerging biofuels industry.

The health promoting benefits of barley consumption have been investigated in animal and human clinical trials. In May 2006, the FDA granted a petition to allow foods containing barley with 0.75 g of Beta-glucan to carry a health claim "barley lowers cholesterol when consumed as part of a healthy diet" (Federal Register 71 (98):29248-29250). When used as a food ingredient, malting or feed barley grain that has a cemented hull (referred to as covered) must be processed to remove that hull. A commonly used processing step known as pearling removes the hull and a substantial portion of the bran and the germ to produce a pearled barley grain, such that at least about 15 to about 40 wt. % of the outer grain is removed. Barley varieties developed especially for food are hulless, i.e., they have a loose hull so do not have to be pearled prior to consumption. Hulless barley must be cleaned as do all grains prior to entering the human food markets, but loose hulls can be removed easily with only slight modifications to the cleaning plants. Food ingredient manufacturers may grind the cleaned barley to produce flour or roll the barley to produce flakes. Food ingredient manufacturers may also utilize the cleaned barley as a whole berry (seed).

SUMMARY OF THE INVENTION

As disclosed herein, there is provided a new barley cultivar designated AS-Wolf. This disclosure relates to the seeds and plants of barley cultivar AS-Wolf, as well as derivatives of the plants of barley cultivar AS-Wolf, and to methods for producing a barley plant produced by crossing the barley cultivar AS-Wolf with itself or another barley cultivar.

Methods such as selfing, backcrossing, hybrid production, crosses to populations, pedigree breeding, and similar methods using the barley cultivar AS-Wolf are disclosed herein. Plants produced using barley cultivar AS-Wolf as at least one parent are also disclosed herein. The barley cultivar AS-Wolf could be used in crosses with other, different barley plants to produce first generation (F1) barley hybrid seeds and plants with additional or superior characteristics. Also included in the present disclosure are the F1 hybrid barley plants grown from the hybrid seed produced by crossing the barley cultivar AS-Wolf to a second barley plant. Still further included in the present disclosure are the seeds of a F1 hybrid plant produced with the barley cultivar AS-Wolf as one parent, the second generation (F2) hybrid barley plant grown from the seed of the F1 hybrid plant, and the seeds of the F2 hybrid plant.

Another aspect of the present disclosure is a method of producing barley seeds comprising crossing a plant of the barley cultivar AS-Wolf to any second barley plant, including itself or another plant of the cultivar AS-Wolf. In some embodiments, the method of crossing can comprise the steps of: (a) planting seeds of the barley cultivar AS-Wolf; (b) cultivating barley plants resulting from the seeds until the plants bear flowers; (c) allowing fertilization of the flowers of the plants; and (d) harvesting seeds produced from the plants.

Another aspect of the present disclosure is a method of producing hybrid barley seeds comprising crossing the barley cultivar AS-Wolf to a second, distinct barley plant that is nonisogenic to the barley cultivar AS-Wolf. In some embodiments, the crossing comprises the steps of: (a) planting seeds of barley cultivar AS-Wolf and a second, distinct barley plant; (b) cultivating the barley plants grown from the seeds until the plants bear flowers; (c) cross-pollinating a flower on one of the two plants with the pollen of the other plant; and (d) harvesting the seeds resulting from the cross pollinating.

Another aspect of the present disclosure is a method for developing a barley plant in a barley breeding program comprising: (a) obtaining a barley plant, or its parts, of the cultivar AS-Wolf; and (b) employing the plant or parts as a source of breeding material using plant breeding techniques. In the method, the plant breeding techniques comprise selfing, backcrossing, hybrid production, crosses to populations, recurrent selection, mass selection, bulk selection, pedigree breeding, or a combination thereof. In some embodiments, the barley plant of cultivar AS-Wolf may be used as the male or female parent.

Another aspect of the present disclosure is a method of producing a barley plant derived from the barley cultivar AS-Wolf, the method comprising the steps of: (a) preparing a progeny plant derived from barley cultivar AS-Wolf by crossing a plant of the barley cultivar AS-Wolf with a second barley plant; and (b) crossing the progeny plant with itself or a second plant to produce a progeny plant of a subsequent generation that is derived from a plant of the barley cultivar AS-Wolf. In one embodiment, the method further comprises: (c) crossing the progeny plant of a subsequent generation with itself or a second plant; and (d) repeating steps (b) and (c) for, in some embodiments, at least 2, 3, 4, or more additional generations to produce an inbred barley plant derived from the barley cultivar AS-Wolf. Also provided by the disclosure is a plant produced by this and the other methods of the disclosure.

In another embodiment, the method of producing a barley plant derived from the barley cultivar AS-Wolf further comprises: (a) crossing the barley cultivar AS-Wolf-derived barley plant with itself or another barley plant to yield additional barley cultivar AS-Wolf-derived progeny barley seed; (b) growing the progeny barley seed of step (a) under plant growth conditions to yield additional barley cultivar AS-Wolf-derived barley plants; and (c) repeating the crossing and growing steps of (a) and (b) to generate further barley cultivar AS-Wolf-derived barley plants. In some embodiments, steps (a) and (b) may be repeated at least 1, 2, 3, 4, 5, or more times as desired. The disclosure further provides a barley plant produced by this and the foregoing methods.

In another aspect, the present disclosure provides regenerable cells for use in tissue culture of barley plant AS-Wolf. The tissue culture can be capable of regenerating plants having essentially all the physiological and morphological characteristics of the barley plant disclosed herein, and of regenerating plants having substantially the same genotype as the barley plant AS-Wolf. The regenerable cells in such tissue cultures can be the head, awn, leaf, pollen, ovule, embryo, cotyledon, hypocotyl, seed, spike, pericarp, meristematic cell, cell, protoplast, root, root tip, pistil, anther, floret, shoot, stem, callus, or a combination thereof. Still further, the present disclosure can provide barley plants regenerated from the tissue cultures of the barley cultivar AS-Wolf.

In a further aspect, the disclosure provides a composition comprising a seed of barley cultivar AS-Wolf comprised in plant seed growth media. In certain embodiments, the plant seed growth media is a soil or synthetic cultivation medium. In specific embodiments, the growth medium may be comprised in a container or may, for example, be soil in a field. Plant seed growth media can provide adequate physical support for seeds and can retain moisture and/or nutritional components.

In a further aspect, the disclosure provides a method of producing a commodity plant product comprising collecting the commodity plant product from the plant of barley cultivar AS-Wolf. In some embodiments, the commodity plant product can be, but is not limited to, grain, flour, bran, baked goods, cereals, pasta, beverages, malts, extractions or medicines. The commodity plant product can comprise at least one cell of barley cultivar AS-Wolf.

In yet another aspect, the disclosure provides a barley plant comprising a single locus conversion of the barley cultivar AS-Wolf, wherein the barley plant is otherwise capable of expressing all the physiological and morphological characteristics of the barley cultivar AS-Wolf. In particular embodiments of the subject innovation, the single locus conversion may comprise a transgenic gene that has been introduced by genetic transformation into the barley cultivar AS-Wolf or a progenitor thereof. In still other embodiments, the single locus conversion may comprise a dominant or recessive allele. The locus conversion may confer potentially any trait upon the single locus converted plant, including, but not limited to, herbicide resistance, insect resistance, resistance to bacterial, fungal, or viral disease, male fertility or sterility, and improved nutritional quality.

In addition to the exemplary aspects and embodiments described above, further aspects and embodiments will become apparent by study of the descriptions that follow.

Definitions

The following definitions are provided:

Allele. An allele is any of one or more alternative forms of a gene that relate to one trait or characteristic. In a diploid cell or organism, the two alleles of a given gene occupy corresponding loci on a pair of homologous chromosomes.

Awn. Awn means the elongated needle-like appendages on the flower-and-seed-bearing "head" at the top of the barley plant. Awns are attached to lemmas. Lemmas enclose the stamen and the stigma as part of the florets. Florets are grouped in spikelets, which in turn together comprise the head or spike.

Backcrossing. Backcrossing is a process in which a breeder repeatedly crosses hybrid progeny back to one of the parents, for example, a first generation hybrid $F_1$ with one of the parental genotypes of the $F_1$ hybrid.

Barley Yellow Dwarf Virus (BYDV). Barley yellow dwarf virus is a viral disease transmitted by aphids. The symptoms include yellow chlorosis of the older leaves, stunting, sterility, and reduced kernel size.

Beta-Glucan Fiber. Beta-glucan fiber is a nonstarch polysaccharide in which individual glucose molecules (20,000-1,000,000) are linked by beta 1-4 and beta 1-3 linkages. Beta-Glucan is the main structural material in the cell walls of barley grain.

Beta-Glucan Fiber Viscosity. Beta-glucan fiber viscosity describes the friction that is created in a solution by the presence of beta-glucan chains (fibers) and is measured in centipoise units.

Beta-Glucan Percentage. Beta-glucan percentage is the percentage of beta-glucan fiber in barley grain. May be reported on either an as-is or dry moisture basis.

Centipoise Units (cps). Centipoise units (cps) are the units commonly used to measure viscosity. By definition the fundamental unit of viscosity measurement is the "Poise", which is a material requiring a sheer stress of one dyne per square centimeter to produce a sheer of one inverse second, which has a viscosity of one poise or 100 centipoise.

Cell. Cell includes a plant cell, whether isolated, in tissue culture, or incorporated in a plant or plant part.

Covered Seed. Barley seed can have a cutin layer that cements the hull (lemma and palea or glumes) to the seed. The hull can only be removed by abrasive processing prior to consumption, known as pearling.

Disease Resistance. Disease resistance or disease resistant is defined as the ability of plants to restrict the activities of a specified disease, such as a fungus, virus, or bacterium.

Disease Tolerance. Disease tolerance or disease tolerant is defined as the ability of plants to endure a specified disease (such as a fungus, virus, or bacterium) or an adverse environmental condition and still perform and produce in spite of this condition.

Essentially All of the Physiological and Morphological Characteristics. A plant having essentially all of the physiological and morphological characteristics means a plant having the physiological and morphological characteristics of the recurrent parent, except for the characteristics derived from the converted trait.

Foliar Disease. Foliar disease is a general term for fungal disease that causes yellowing or browning or premature drying of the leaves. The disease typically involves *Septoria*, net blotch, spot blotch, or scald.

Grain yield. Grain yield, also known as crop yield, is the measure of the yield of a crop per unit area of land cultivated and the seed generation of the plant itself.

Head. Head refers to a group of spikelets at the top of one plant stem. The term "spike" also refers to the head of a barley plant located at the top of one plant stem.

Herbicide Resistance. Herbicide resistance or herbicide resistant is defined as the ability of plants to survive and reproduce following exposure to a dose of herbicide that would normally be lethal to the plant.

Herbicide Tolerance. Herbicide tolerance or herbicide tolerant is defined as the ability of plants to survive and reproduce after herbicide treatment.

Homozygous Plant. A homozygous plant is defined as a plant with homozygous genes at 95% or more of its loci.

Hulless Seed. Barley seed can have a cutin layer that cements the hull (lemma and palea or glumes) to the seed. The absence of a cutin layer is referred to as hulless. The loose hull can be easily removed at harvest or by minimal cleaning/processing prior to consumption. This has also been referred to as naked or nude seed.

Inbred. Inbred refers to a homozygous plant or a collection of homozygous plants.

Insect Resistance. Insect resistance or insect resistant is defined as the ability of plants to restrict the activities of a specified insect or pest.

Insert Tolerance. Insect tolerance or insect tolerant is defined as the ability of plants to endure a specified insect or pest and still perform and produce in spite of the insect or pest.

Iodine Stain—IKI—Iodine/Potassium Iodide Stock Solution for Starch Test. The stock solution of iodine stain for the starch test consists of 35 g of KI (potassium iodide) and 5 g of I (Iodine) in 500 ml of distilled water. The working solution consists of a 1:3 dilution of the stock with distilled water (1:3=one part stock and three parts water).

Iodine or Starch Test. The iodine or starch test tests for the absence or reduced levels of amylose in a plant part, most often the seed. The absence or reduced levels of amylose can be detected by cutting the nonembryo end of the seed at the dough stage and staining with a dilute iodine (IKI) stain. Amylose stains blue while amylopectin stains brown.

Leaf Rust. A fungal disease that results in orange-red pustules on the leaf surface. Caused by *Puccinia hordei*.

Lodging. Lodging refers to the bending or breakage of the plant stem, or the tilting over of the plant, which complicates harvest and can diminish the value of the harvested product.

Net blotch. Net blotch refers to a fungal disease that appears as elongated black lesions running parallel to the leaf veins with distinctive, dark brown net-like patterns. Net blotch is caused by *Pyrenophora teres*.

Percent Identity. Percent identity refers to the comparison of the homozygous alleles of two barley varieties. Percent identity is determined by comparing a statistically significant number of the homozygous alleles of two developed varieties. For example, a percent identity of 90% between barley variety 1 and barley variety 2 means that the two varieties have the same allele at 90% of their loci.

Percent Similarity. Percent similarity refers to the comparison of the homozygous alleles of a barley variety such as AS-Wolf with another plant, and if the homozygous allele of AS-Wolf matches at least one of the alleles from the other plant then they are determined to be similar. Percent similarity is determined by comparing a statistically significant number of loci and recording the number of loci with similar alleles as a percentage. A percent similarity of 90% between AS-Wolf and another plant means that AS-Wolf matches at least one of the alleles of the other plant at 90% of the loci.

Plant. Plant includes an immature or mature whole plant, including a plant from which seed, grain, or anthers have been removed. A seed or embryo that will produce the plant is also considered to be a plant.

Plant Height (Hgt). Plant height is the average height in inches or centimeters of a group of plants, as measured from the ground level to the tip of the head, excluding awns.

Plant Parts. Plant parts (or reference to "a barley plant, or a part thereof") includes but is not limited to protoplasts, callus, leaves, stems, roots, root tips, anthers, pistils, seeds, grain, pericarps, embryos, pollen, ovules, cotyledons, hypocotyls, spikes, florets, awns, lemmas, shoots, tissues, petioles, cells, meristematic cells, or a combination thereof.

Powdery Mildew. Powdery mildew refers to a fungal disease that results in white to gray powdery pustules on the leaf blade with associated yellowing and browning. Powdery mildew is caused by *Blumeria graminis* f. sp. *hordei*.

Progeny. Progeny includes an F1 barley plant produced from the cross of two barley plants where at least one plant includes barley cultivar AS-Wolf. Progeny further includes but is not limited to subsequent F2, F3, F4, F5, F6, F7, F8, F9, and F10 generational crosses with the recurrent parental line.

Quantitative Trait Loci (QTL). Quantitative trait loci refer to genetic loci that control to some degree numerically representable traits that are usually continuously distributed.

Scab. Scab refers to a fungal disease that causes salmon-orange spore masses at the base of the glumes and on the seed. It may also cause shriveling of seed. Scab is caused by *Fusarium graminearum*.

Scald. Scald refers to a fungal disease that causes spots to develop on the leaves during cool, wet weather. The spots are oval shaped and the margins of the spots change from bluish-green to zonated brown or tan rings with bleached straw-colored centers. Scald is caused by *Rhynchosporium secalis*. Septoria. Septoria refers to a fungal disease that appears as elongated, light brown spots on the leaves. It is caused by *Septoria passerinii*.

Single Gene Converted (Conversion). Single gene converted (conversion) plants refers to plants that are developed by a plant breeding technique called backcrossing wherein essentially all of the desired morphological and physiological characteristics of a variety are recovered in addition to the single gene transferred into the variety via the backcrossing technique or via genetic engineering.

Smut, covered. Covered smut refers to a fungal disease in which masses of black spores replace the seed kernels on the head. A persistent membrane can be ruptured during harvest to disperse spores. Covered smut is caused by *Ustilago hordei*.

Smut, loose. Loose smut refers to a fungal disease in which masses of black spores replace the seed kernels on the head. The thin membrane that covers the spores is easily ruptured and spores are disbursed by wind. Loose smut is caused by *Ustilago nuda*.

Spot Blotch. Spot blotch refers to a fungal disease that appears as dark, chocolate-colored blotches forming irregular dead patches on the leaves. Spot blotch is caused by *Cochliobolus sativus*.

Stem rust. Stem rust refers to a fungal disease that produces masses of brick-red pustules on stems and leaf sheaths. Stem rust can be caused by either *Puccinia graminis* f. sp. *tritici* or *Puccinia graminis* f. sp. *secalis*.

Stripe Rust. Stripe rust refers to a fungal disease that results in light yellowish orange pustules arranged in stripes between the veins of the leaves. Stripe rust is caused by *Puccinia striiformis* f. sp. *hordei*.

Waxy Bloom. A waxy or powdery whitish to bluish coating that can be found on the surface of stems, leaves, and spikes. Plant parts that do not have wax are referred to as "glossy." A synonym for presence of the wax is "glaucous."

Waxy Seed. The endosperm of waxy seed contains starch granules with low amylose content. The lower amylose results in seed having an opaque appearance and can be confirmed using the Iodine test.

Waxy Starch. Starch in grain is stored in granules that can be made of varying amounts of amylopectin (branched) and amylose (straight chained) starch. Waxy starch in barley has low amylose content ranging from 0 to 20%. Amylose content in the starch granules is genetically controlled by one or more alleles at the Wax locus on chromosome 1 (7H) which encodes the production of granule-bound starch synthase. The homozygous recessive wax wax genotype has starch granules with low amounts of amylose.

DETAILED DESCRIPTION OF THE INVENTION

In the following description, for purposes of explanation, numerous specific details are set forth in order to provide a thorough understanding of the subject innovation. It may be evident, however, that the claimed subject matter may be practiced without these specific details.

One or more examples of the subject innovation are set forth below. Each example is provided by way of explanation of the innovation, not a limitation of the innovation. It will be apparent to those skilled in the art that various modifications and variations may be made to the present innovation without departing from the scope or spirit of the innovation. For instance, features illustrated or described as part of one embodiment can be used on another embodiment to yield a still further embodiment.

Thus, it is intended that the present innovation covers such modifications and variations as come within the scope of the appended claims and their equivalents. Other objects, features, and aspects of the present innovation are disclosed in or are obvious from the following detailed description. It is to be understood by one of ordinary skill in the art that the present discussion is a description of exemplary embodiments only and is not intended as limiting the broader aspects of the present innovation.

In an embodiment, the innovation is directed to barley cultivar AS-Wolf, its seeds, plants, and hybrids. The presently disclosed cultivar AS-Wolf can show uniformity and stability for all traits, as described below. The barley AS-Wolf has been self-pollinated a sufficient number of generations, with attention to uniformity of plant type to ensure homozygosity and phenotypic stability. The cultivar has been increased with continued observation for uniformity in appearance and performance. AS-Wolf may contain variants at frequencies of up to 100/10,000 seed (1.0%) including tall plants (roughly 2-4 centimeters taller), covered seed, or nonwaxy seed. No other variants are known to occur and AS-Wolf is a stable and uniform variety in appearance and performance.

AS-Wolf is a waxy starch, six-row barley variety created by crossing "Tamalpais" with "P16Y8060." Tamalpais (PI 645477) is a spring, six-row, hulless, long-awned barley with normal starch (25% amylose) released by the University of California Agricultural Experiment Station. P16Y8060 is a spring, six-row, hulless, waxy starch barley breeding line developed by Phoenix Seed, Inc. with the pedigree, Wanubet/Lacey//Rasmusson. With each generation F6 to F9, AS-Wolf exhibited uniformity and stability. The breeding history of AS-Wolf is summarized in Table 1.

TABLE 1

Breeding History of AS-Wolf

| Year, Season | Location | Seed Generation Planted | Selection |
| --- | --- | --- | --- |
| 2017, January | Growth Chambers, Fargo, ND | Cross | Tamalpais × P16Y8060 |
| 2017, March | Growth Chambers, Fargo, ND | F1 | Verify cross, uniformity of F1 plants, heads segregating for opaque and vitreous seed. |
| 2017, May-June | Casselton, ND | F2 | Select plant phenotype similar to Tamalpais & starch type, waxy using iodine stain red vs. non-waxy, dark blue |
| 2017, August | Growth Chambers, Fargo, ND | F3 | Plant as head rows; same selection as F2. |
| 2017, November | Yuma, AZ and California, central valley | F4 | Plant as head rows; same selection as F2, F3; evaluate for uniformity, Barley Yellow Dwarf Virus and powdery mildew tolerance/resistance in California; harvest individual plants. |
| 2018, Summer | Casselton, ND | F5 | 100 plant selections planted as plots with 1-3 replications. Families (selections from same F3 head row) evaluated for uniformity, maturity, height, and yield. One selection was designated Y039-1. |
| 2018, November | California, central valley | F6 | Selections planted as head rows, in yield tests and small bulk increases. Selection for stripe rust and Barley yellow dwarf virus tolerance/resistance along with yield, standability, and maturity. |

TABLE 1-continued

Breeding History of AS-Wolf

| Year, Season | Location | Seed Generation Planted | Selection |
|---|---|---|---|
| 2019, Summer | Casselton, ND and California, central valley | F7 | Y039-1 selected for yield tests in ND and Breeder seed increase in California |
| 2019, November | California, central valley | F8 | Y039-1 testing and increase as a second Breeder Seed increase California |
| 2020, November | California, central valley | F9 | Y039-1 testing and increase as Foundation seed; Line renamed AS-Wolf. |

AS-Wolf is most similar in appearance to the variety Tamalpais. However, AS-Wolf has waxy starch (less than 15% amylose) while Tamalpais has normal starch (25% or more amylose). AS-Wolf has higher yield and test weight than Tamalpais. These differences were observed across 5 station years between 2018 and 2021.

Some physical characteristics of AS-Wolf are listed in Table 2. AS-Wolf can be characterized by a six-rowed, oblong, mid-dense spike and the seed of AS-Wolf can be short, and hulless, all like Tamalpais. However, the rachis edge of AS-Wolf can be lacking hairs while Tamalpais rachis edge can have hairs. The glume awn surface of AS-Wolf can be smooth while the glume awn surface of Tamalpais can be rough. The lemma of AS-Wolf can have long awns that are semi-smooth. The lemma of Tamalpais can have long awns that are rough. Rachilla hairs of AS-Wolf can be short while rachilla hairs of Tamalpais can be long. Additional identifying characteristics of AS-Wolf are provided below in Table 2.

TABLE 2

Plant and Seed Characteristics of AS-Wolf

| Plant | |
|---|---|
| Growth Habit | Spring |
| Spike | Six-row |
| Juvenile Growth Habit | Semi-Erect |
| Plant Tillering | Intermediate |
| Maturity (50% flowering) | Averages 80 days after planting: 3.5 days earlier than Tamalpais in California |
| Plant Height | Short; averages 68.69 cm; 2.6 cm shorter than Tamalpais in California |
| Stem | |
| Exsertion (flag to spike at maturity) | Slight |
| Stem Color at Maturity | White |
| Anthocyanin | Absent |
| Number of Nodes (Originating from Node Above Ground) | 5 |
| Collar Shape | V-Shaped |
| Neck Shape | Straight |
| Leaves | |
| Coleoptile Color | Green |
| Basal Leaf Sheath Pubescence at Seedling Stage | Absent |
| Basal Leaf Sheath Color | Green |
| Leaf Color at Boot | Green |
| Flag Leaf at Boot | Erect |
| Flag Leaf at Boot | Not Twisted |
| Flag Leaf at Boot | Waxy Bloom |
| Pubescence on Leaf (first leaf below flag leaf) Blade | Absent |
| Pubescence on Leaf (first leaf below flag leaf) Sheath | Absent |

TABLE 2-continued

Plant and Seed Characteristics of AS-Wolf

| | |
|---|---|
| Auricle Color | White |
| Pubescence on Auricle | Absent |
| Waxiness | Slightly waxy |
| Width (First Leaf Below Flag Leaf) | 12.7 mm |
| Length (First Leaf Below Flag Leaf) | 14.5 cm |
| Anthocyanin in Leaf Sheath | Absent |
| Spike | |
| Shape | Oblong |
| Density | Mid-Dense |
| Position at Maturity | Erect |
| Waxy Bloom | Slightly waxy |
| Lateral Kernels Overlap | None |
| Hairiness of Rachis Edge | Lacking |
| Lemma | |
| Awns | Straight |
| Awn Length | Long |
| Awn Surface | Semi-smooth |
| Teeth | Absent |
| Hair | Absent |
| Shape of Base | Transverse crease |
| Rachilla Hairs | Short |
| Glumes | |
| Length | One-half of Lemma |
| Hairiness | None |
| Length of Hairs | None |
| Glume Awn Length Relative to Glume Length | Equal |
| Glume Awn Surface | Smooth |
| Stigma | |
| Hairs | Few |
| Seed | |
| Hull Type (Lemma/Palea Adherence) | Hulless (naked) |
| Hairs on Ventral Furrow | Absent |
| Kernel Aleurone Color | Colorless |
| Kernel Length | Short (8-9 mm) |
| Wrinkling of Hull | Naked |
| Average 1,000 Kernel Weight | 36 g |
| Starch | Waxy (stains red with IKI) |

This disclosure is also directed to a composition comprising a seed of AS-Wolf comprised in plant seed growth media. Plant seed growth media can provide adequate physical support for seeds and can retain moisture and/or nutritional components. In embodiments, the plant seed growth media can be a soil or synthetic cultivation medium. In some embodiments, the growth medium may be comprised in a container or may, for example, be soil in a field.

This disclosure is also directed to methods for producing a barley variety by crossing a first parent barley variety with a second parent barley variety, wherein the first or second barley variety is the variety AS-Wolf. Therefore, any methods using the barley variety AS-Wolf are part of this disclosure, including selfing, backcrossing, hybrid production, crosses to populations, recurrent selection, mass selection, bulk selection, pedigree breeding, mutagenesis, and transgenic modification. Any plants produced using barley variety AS-Wolf as a parent are within the scope of this disclosure.

Further reproduction of the barley variety AS-Wolf can occur by tissue culture and regeneration to produce barley plants capable of having the physiological and morphological characteristics of barley variety AS-Wolf.

A further embodiment of the present disclosure is a backcross conversion of barley variety AS-Wolf. A backcross conversion occurs when DNA sequences are introduced through non-transformation breeding techniques, such as backcrossing. Desired traits transferred through this process include, but are not limited to, higher grain yield, shorter plant height, and increased beta-glucan percentage. The trait of interest can be transferred from the donor parent to the recurrent parent, in this case, the barley plant disclosed herein. Single gene traits may result from either the transfer of a dominant allele or a recessive allele. Selection of progeny containing the trait of interest can be done by direct selection for a trait associated with a dominant allele. Selection of progeny for a trait that is transferred via a recessive allele may require growing and selfing the first backcross to determine which plants carry the recessive alleles. Recessive traits may require additional progeny testing in successive backcross generations to determine the presence of the gene of interest.

Another embodiment of this disclosure is a method of developing a backcross conversion AS-Wolf barley plant that can involve the repeated backcrossing to barley variety AS-Wolf. The number of backcrosses made may be 2, 3, 4, 5, 6, or greater, and the specific number of backcrosses used will depend upon the genetics of the donor parent and whether molecular markers are utilized in the backcrossing program. Using backcrossing methods, one of ordinary skill in the art can develop individual plants and populations of plants that retain at least 70%, 75%, 79%, 80%, 81%, 82%, 83%, 84%, 85%, 86%, 87%, 88%, 89%, 90%, 91%, 92%, 93%, 94%, 95%, 96%, 97%, 98%, or 99% of the genetic profile of barley variety AS-Wolf. The percentage of the genetics retained in the backcross conversion may be measured by either pedigree analysis or through the use of genetic techniques such as molecular markers or electrophoresis.

In pedigree analysis, on average 50% of the starting germplasm could be passed to the progeny line after one cross to another line, 75% after backcrossing once, 87.5% after backcrossing twice, and so on. Molecular markers could also be used to confirm and/or determine the recurrent parent used. The backcross conversion developed from this method may be similar to AS-Wolf for the results listed in Table 1. Such similarity may be measured by a side by side phenotypic comparison. Any such comparison should be made in environmental conditions that account for the trait being transferred.

Another embodiment of the disclosure is an essentially derived variety of AS-Wolf. Essentially derived varieties may be obtained for example by the selection of a natural or induced mutant, or of a somaclonal variant, the selection of a variant individual from plants of the initial variety, or backcrossing. An essentially derived variety of AS-Wolf may further be considered as one whose production requires the repeated use of variety AS-Wolf or is predominately derived from variety AS-Wolf.

This disclosure is also directed to methods for using barley variety AS-Wolf in plant breeding. One such embodiment is the method of crossing barley variety AS-Wolf with another variety of barley to form a first generation population of F1 plants. This disclosure also includes the population of first generation F1 plants produced by this method. This first generation population of F1 plants may comprise a substantially complete set of the alleles of barley variety AS-Wolf. One of ordinary skill in the art may utilize either breeder books or molecular methods to identify a particular F1 plant produced using barley variety AS-Wolf. These embodiments also include use of backcross conversions of barley variety AS-Wolf to produce first generation F1 plants.

A method of developing AS-Wolf-progeny barley plants comprising crossing AS-Wolf with a second barley plant and performing a breeding method is also disclosed herein. One of ordinary skill in the art may cross barley variety AS-Wolf with another variety of barley. The F1 seed derived from this cross may be grown to form a homogeneous population. The F1 seed may contain one set of the alleles from variety AS-Wolf and one set of the alleles from the other barley variety. The F1 genome may be made up of 50% variety AS-Wolf and 50% of the other variety. The F1 seed may be grown and allowed to self, thereby forming F2 seed. On average, the F2 seed may have derived 50% of its alleles from variety AS-Wolf and 50% from the other barley variety, but various individual plants from the population may have a greater percentage of their alleles derived from AS-Wolf. The F2 seed may be grown and selection of plants may be made based on visual observation and/or measurement of traits. The AS-Wolf-derived progeny that exhibit one or more of the desired AS-Wolf-derived traits may be selected and each plant may be harvested separately. This F3 seed from each plant may be grown in individual rows and allowed to self. Then selected rows or plants from the rows may be harvested and threshed individually. The selections may again be based on visual observation and/or measurements for desirable traits of the plants, such as one or more of the desirable AS-Wolf-derived traits. The process of growing and selection may be repeated any number of times until a homozygous AS-Wolf-derived barley plant is obtained. The homozygous AS-Wolf-derived barley plant may contain desirable traits derived from barley variety AS-Wolf, some of which may not have been expressed by the other original barley variety to which barley variety AS-Wolf was crossed and some of which may have been expressed by both barley varieties but now would be at a level equal to or greater than the level expressed in barley variety AS-Wolf. The homozygous AS-Wolf-derived barley plants may have, on average, 50% of their genes derived from barley variety AS-Wolf, but various individual plants from the population may have a greater percentage of their alleles derived from AS-Wolf. The breeding process of crossing, selfing, and selection may be repeated to produce another population of AS-Wolf-derived barley plants with, on average, 25% of their genes derived from barley variety AS-Wolf, but various individual plants from the population may have a greater percentage of their alleles derived from AS-Wolf. Another embodiment of the disclosure is homozygous AS-Wolf-derived barley plants that have received AS-Wolf-derived traits.

The previous example can be modified in numerous ways. For instance, selection may occur at every selfing generation; selection may occur before or after the actual self-pollination process occurs; or individual selections may be made by harvesting individual spikes, plants, rows, or plots at any point during the breeding process described herein. In addition, double haploid breeding methods may be used at any step in the process. The population of plants produced at each and any generation of selfing is also described herein, and each such population may consist of plants containing approximately 50% of its genes from barley variety AS-Wolf, 25% of its genes from barley variety AS-Wolf in the second cycle of crossing, selfing, and selection, 12.5% of its genes from barley variety AS-Wolf in the third cycle of crossing, selfing, and selection, and so on.

Another embodiment of this disclosure is the method of obtaining a homozygous AS-Wolf-derived barley plant by crossing barley variety AS-Wolf with another variety of barley and applying double haploid methods to the F1 seed or F1 plant or to any generation of AS-Wolf-derived barley obtained by the selfing of this cross.

Still further, this disclosure is directed to methods for producing AS-Wolf-derived barley plants by crossing barley variety AS-Wolf with a barley plant and growing the progeny seed, and repeating the crossing or selfing along with the growing steps with the AS-Wolf-derived barley plant from 1 to 2 times, 1 to 3 times, 1 to 4 times, or 1 to 5 times. Thus, any and all methods using barley variety AS-Wolf in breeding are part of this disclosure, including selfing, backcrossing, hybrid production, crosses to populations, recurrent selection, mass selection, bulk selection, and pedigree breeding. Unique starch profiles, molecular marker profiles, and/or breeding records can be used by those of ordinary skill in the art to identify the progeny lines or populations derived from these breeding methods.

Still further, this disclosure is directed to methods for producing AS-Wolf-derived barley plants by pedigree breeding. Pedigree breeding starts with the crossing of two genotypes, such as AS-Wolf and another barley variety having one or more desirable characteristics that is lacking or that complements AS-Wolf. If the two original parents do not provide all the desired characteristics, other sources can be included in the breeding population. In the pedigree breeding method, plants exhibiting desired traits are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: F1 to F2; F2 to F3; F3 to F4; F4 to F5; etc. After a sufficient amount of inbreeding, successive filial generations can serve to increase seed of the developed variety. In an embodiment, the developed variety comprises homozygous alleles at about 95% or more of its loci.

In addition, this disclosure encompasses progeny with the same or greater grain yield of AS-Wolf, the same or shorter plant height, and the same or more beta-glucan percentage of AS-Wolf. The expression of these traits may be measured by agronomic performance testing. Any such comparison should be made in the same environmental conditions.

This disclosure is also directed to a transgenic variant of AS-Wolf. A transgenic variant of AS-Wolf may contain at least one transgene but could contain at least 1, 2, 3, 4, 5, 6, 7, 8, 9, 10, or more transgenes. In another embodiment, a transgenic variant of AS-Wolf may contain no more than 15, 14, 13, 12, 11, 10, 9, 8, 7, 6, 5, 4, 3, or 2 transgenes. Another embodiment of the disclosure involves a process for producing barley cultivar AS-Wolf further comprising a desired trait. The process can comprise introducing a transgene that confers a desired trait to a barley plant of cultivar AS-Wolf. As part of the disclosure, one of ordinary skill in the art may utilize any method of producing transgenic plants that is currently known or yet to be developed.

In another embodiment, the method may involve the creation of variants by mutagenesis or transformation of barley cultivar AS-Wolf. All plants produced using barley cultivar AS-Wolf as at least one parent are considered within the scope of this disclosure.

The present disclosure also provides for single or multiple gene converted plants of barley cultivar AS-Wolf. The transferred gene(s) may be a dominant or recessive allele. The transferred gene(s) may confer such traits as herbicide tolerance or resistance, insect tolerance or resistance, tolerance or resistance to bacterial, fungal, or viral disease, male fertility, male sterility, enhanced nutritional quality, modified fatty acid metabolism, modified carbohydrate metabolism, modified seed yield, modified protein percent, modified beta-glucan percent, modified lodging resistance, modified lipoxygenase, beta-glucanase and/or polyphenol oxidase content and/or activity, and/or industrial usage, or a combination thereof. The gene may be a naturally occurring barley gene or a transgene introduced through genetic engineering techniques.

Any method for plant transformation known in the art may be utilized in the present innovation. The disclosure comprises transgenic methods including, but not limited to, expression vectors introduced into plant tissues using a direct gene transfer method such as microprojectile-mediated delivery, DNA injection, electroporation and the like. In an embodiment, expression vectors may be introduced into plant tissues by using either microprojectile-mediated delivery with a biolistic device or by using *Agrobacterium*-mediated transformation. Transformed plants obtained with the protoplasm of barley cultivar AS-Wolf are intended to be within the scope of this disclosure.

Various genetic elements can be introduced into the plant genome using transformation. These elements include but are not limited to genes, coding sequences, inducible, constitutive, and tissue-specific promoters, enhancing sequences and signal, and targeting sequences.

In embodiments, a genetic trait that has been engineered into a barley AS-Wolf plant using transformation techniques could then be moved into another line using traditional breeding techniques that are known in the plant breeding arts. For example, a backcrossing approach could be used to move a transgene from a transformed barley AS-Wolf plant to another barley variety and the resulting progeny would comprise a transgene.

Likewise, in an embodiment, agronomic genes can be expressed in transformed AS-Wolf plants. More particularly, plants can be genetically engineered to express various phenotypes of agronomic interest. Through the transformation of AS-Wolf plants, the expression of genes can be modulated to enhance disease tolerance or resistance, insect tolerance or resistance, herbicide tolerance or resistance, water stress tolerance, agronomic traits, and/or grain quality traits, for example. Transformation can also be used to insert DNA sequences that control or help control male sterility. DNA sequences native to barley as well as nonnative DNA sequences can be transformed into barley and used to modulate levels of native or nonnative proteins. Antisense technology, various promoters, targeting sequences, enhancing sequences, and other DNA sequences can be inserted into the AS-Wolf barley genome for the purpose of modulating the expression of proteins. Exemplary genes that can be inserted into the AS-Wolf barley genome as part of the present disclosure include, but are not limited to, those categorized below.

(1) Genes that Confer Tolerance or Resistance to Pests or Disease
(A) Plant disease resistance genes. Plant defenses are often activated by specific interaction between the product of a disease resistance gene (R) in the plant and the product of a corresponding avirulence (Avr) gene in the pathogen. In embodiments, a AS-Wolf plant variety can be transformed with a cloned resistance gene to engineer plants that are tolerant or resistant to specific pathogen strains.
(B) *Fusarium* head blight along with deoxynivalenol both produced by the pathogen *Fusarium graminearum* Schwabe have caused devastating losses in barley production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome inactivating proteins, flavonoids, and lactoferricin. During infection with *Fusarium graminearum*, deoxynivalenol is produced. There is evidence that production of deoxynivalenol increases the virulence of the disease. Genes with properties for detoxification of deoxynivalenol have been engineered for use in barley. A synthetic peptide that competes with deoxynivalenol has also been identified. Changing the ribosomes of the host so that they have reduced affinity for deoxynivalenol has also been used to reduce the virulence of *Fusarium graminearum.*

(C) Genes used to help reduce *Fusarium* head blight include, but are not limited to, Tri101 (*Fusarium*), PDR5 (yeast), tlp-1 (oat), tlp-2 (oat), leaf tlp-1 (wheat), tip (rice), tlp-4 (oat), endochitinase, exochitinase, glucanase (*Fusarium*), permatin (oat), seed hordothionin (barley), alpha-thionin (wheat), acid glucanase (alfalfa), chitinase (barley and rice), class beta Il-1,3-glucanase (barley), PR5/tlp (*Arabidopsis*), zeamatin (maize), type 1 RIP (barley), NPR1 (*Arabidopsis*), lactoferrin (mammal), oxalyl-CoA-decarboxylase (bacterium), IAP (baculovirus), ced-9 (*C. elegans*), and glucanase (rice and barley).

(2) A gene conferring tolerance or resistance to a pest.

(A) A gene conferring resistance to such diseases as barley rusts, *Septoria tritici, Septoria nodorum*, powdery mildew, *Helminthosporium* diseases, smuts, bunts, *Fusarium* diseases, bacterial diseases, and viral diseases.

(B) A *Bacillus thuringiensis* protein, a derivative thereof, or a synthetic polypeptide modeled thereon.

(C) An insect-specific hormone or pheromone such as an ecdysteroid or juvenile hormone, a variant thereof, a mimetic based thereon, or an antagonist or agonist thereof.

(D) An insect-specific peptide that, upon expression, disrupts the physiology of the affected pest.

(E) An enzyme responsible for hyperaccumulation of a monoterpene, a sesquiterpene, a steroid, hydroxamic acid, a phenylpropanoid derivative, or another non-protein molecule with insecticidal activity.

(F) An enzyme involved in the modification, including the post-translational modification, of a biologically active molecule. For example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and/or a glucanase, whether natural or synthetic.

(G) A molecule that stimulates signal transduction.

(H) A hydrophobic moment peptide.

(I) A membrane permease, a channel former, or a channel blocker.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses.

(K) An insect-specific antibody or an immunotoxin derived therefrom. Thus, an antibody targeted to a critical metabolic function in the insect gut would inactivate an affected enzyme, killing the insect.

(L) A virus-specific antibody.

(M) A developmental-arrestive protein produced in nature by a pathogen or a parasite. For example, fungal endo-alpha-1,4-D-polygalacturonases facilitate fungal colonization and plant nutrient release by solubilizing plant cell wall homoalpha-1,4-D-galacturonase.

(N) A developmental-arrestive protein produced in nature by a plant.

(O) Genes involved in the Systemic Acquired Resistance response and/or pathogenesis-related genes.

(P) Antifungal genes.

(Q) Detoxification genes, such as for fumonisin, beauvericin, moniliformin, zearalenone, and their structurally related derivatives.

(R) Cystatin and cysteine proteinase inhibitors.

(S) Defensin genes.

(T) Genes conferring resistance to nematodes.

(3) Genes that Confer Tolerance or Resistance to an Herbicide, for example:

(A) Acetohydroxy acid synthase. Acetohydroxy acid synthase, which has been found to make plants that express this enzyme resistant to multiple types of herbicides, has been introduced into a variety of plants. Other genes that confer tolerance to herbicides include: a gene encoding a chimeric protein of rat cytochrome P4507A1 and yeast NADPH-cytochrome P450 oxidoreductase, genes for glutathione reductase and superoxide dismutase, and genes for various phosphotransferases.

(B) An herbicide that inhibits the growing point or meristem, such as an imidazolinone or a sulfonylurea.

(C) Glyphosate (resistance imparted by mutant 5-enolpyruvl-3-phosphoshikimate synthase (EPSP) and aroA genes, respectively) and other phosphono compounds such as glufosinate (phosphinothricin acetyl transferase (PAT) and *Streptomyces hygroscopicus* PAT (bar) genes), and pyridinoxy or phenoxy proprionic acids and cyclohexones (ACCase inhibitor-encoding genes). Glyphosate resistance is also imparted to plants that express a gene that encodes a glyphosate oxido-reductase enzyme. In addition, glyphosate resistance can be imparted to plants by the over-expression of genes encoding glyphosate N-acetyltransferase. Exemplary genes conferring resistance to phenoxy proprionic acids and cyclohexones, such as sethoxydim and haloxyfop, are the Accl-S1, Accl-S2, and Accl-S3 genes.

(D) An herbicide that inhibits photosynthesis, such as a triazine (psbA and gs+ genes) and a benzonitrile (nitrilase gene).

(E) Protoporphyrinogen oxidase (protox). Protox is necessary for the production of chlorophyll, which is necessary for all plant survival. The protox enzyme serves as the target for a variety of herbicidal compounds. These herbicides also inhibit growth of all the different species of plants present, causing their total destruction.
(4) Genes that Confer or Improve Grain Quality, for example:
(A) Genes that alter fatty acids. For example, fatty acids may be altered by: (1) down-regulation of stearyl-ACP desaturase to increase stearic acid content of the plant, by for example, transforming a plant with a nucleic acid encoding an anti-sense of stearyl-ACP desaturase; (2) elevating oleic acid via FAD-2 gene modification and/or decreasing linolenic acid via FAD-3 gene modification; (3) altering conjugated linolenic or linoleic acid content; and/or (4) altering LEC1, AGP, Dek1, Superall, mi1ps, and various Ipa genes such as Ipa1, Ipa3, hpt or hggt.
(B) Genes that alter phosphorus content. For example, phosphorus content may be altered by: (1) introduction of a phytase-encoding gene, which would enhance breakdown of phytate and add more free phosphate to the transformed plant; and/or (2) up-regulation of a gene that reduces phytate content.
(C) Genes that alter carbohydrates. This can be effected, for example, by altering a gene for an enzyme that affects the branching pattern of starch or a gene altering thioredoxin *Bacillus subtilis* levansucrase gene.
(D) Altered antioxidant content or composition, such as alteration of tocopherol or tocotrienols.
(E) Altered essential seed amino acids.
(5) Genes that Control Male Sterility:
(A) There are several methods of conferring genetic male sterility available, such as multiple mutant genes at separate locations within the genome that confer male sterility. In addition to these methods, a system of nuclear male sterility may be used, which system includes: identifying a gene that is critical to male fertility; silencing this gene; removing the native promoter from the gene and replacing it with an inducible promoter; inserting this genetically engineered gene back into the plant; and creating a plant that is male sterile because the inducible promoter is not "on," resulting in the male fertility gene not being transcribed. Fertility may be restored by inducing, or turning "on," the promoter, which in turn allows the gene that confers male fertility to be transcribed:
(B) Introduction of a deacetylase gene under the control of a tapetum-specific promoter and with the application of the chemical Ni—Ac-PPT.
(C) Introduction of various stamen-specific promoters.
(D) Introduction of the bamase and the barstar genes.
(6) Genes that Create a Site for Site Specific DNA Integration. This includes the introduction of FRT sites that may be used in the FLP/FRT system and/or Lox sites that may be used in the Cre/Loxp system. Other systems that may be used include the Gin recombinase of phage Mu, the Pin recombinase of *E. coli*, and the R/RS system of the pSRi plasmid.
(7) Genes that Affect Abiotic Stress Resistance
(A) Genes that affect abiotic stress resistance (including but not limited to flowering, seed development, enhancement of nitrogen utilization efficiency, altered nitrogen responsiveness, drought resistance or tolerance, cold resistance or tolerance, and salt resistance or tolerance) and increased yield under stress. For example, water use efficiency can be altered through alteration of malate. In addition, various genes, including CBF genes and transcription factors, can be effective in mitigating the negative effects of freezing, high salinity, and drought on plants, as well as conferring other positive effects on plant phenotype. Abscisic acid can be altered in plants, resulting in improved plant phenotype, such as increased yield and/or increased tolerance to abiotic stress. Cytokinin expression can be modified resulting in plants with increased stress tolerance, such as drought tolerance, and/or increased yield. Nitrogen utilization can be enhanced and/or nitrogen responsiveness can be altered. Ethylene can be altered. Plant transcription factors or transcriptional regulators of abiotic stress can also be altered.
(B) Improved tolerance to water stress from drought or high salt water condition.
(C) Improved water stress tolerance through increased mannitol levels via the bacterial mannitol-1-phosphate dehydrogenase gene.
(8) Other genes and transcription factors that affect plant growth and agronomic traits such as yield, flowering, plant growth, lodging, and/or plant structure, can be introduced or introgressed into plants.
(9) Genes that Confer Agronomic Enhancements, Nutritional Enhancements, or Industrial Enhancements
(10) Genes that alter enzyme activity for improved disease resistance and/or improved plant or grain quality may be introduced or introgressed into plants. For example, lipoxygenase levels can be altered to improve disease resistance and/or to improve the quality of the grain, resulting in improved flavor for beer, cereal, and other food products made from the grain. Another enzyme whose activity can be altered is beta-glucanase for improved plant and/or grain quality. Yet another enzyme whose activity can be altered is polyphenol oxidase for improved plant and/or grain quality.

Methods for Barley Transformation

Numerous methods for plant transformation have been developed, including biological and physical plant transformation protocols. In addition, expression vectors and in vitro culture methods for plant cell or tissue transformation and regeneration of plants are available.

*Agrobacterium*-Mediated Transformation. One method for introducing an expression vector into plants is based on the natural transformation system of *Agrobacterium*. *A. tumefaciens* and *A. rhizogenes*, which are plant pathogenic soil bacteria that genetically transform plant cells. The Ti and Ri plasmids of *A. tumefaciens* and *A. rhizogenes*, respectively, carry genes responsible for genetic transformation of the plant.

Direct Gene Transfer. Several methods of plant transformation, collectively referred to as direct gene transfer, have been developed as an alternative to *Agrobacterium*-mediated transformation. A generally applicable method of plant transformation is microprojectile-mediated transformation, wherein DNA is carried on the surface of microprojectiles measuring 1 to 4 pm. The expression vector is introduced into plant tissues with a biolistic device that accelerates the microprojectiles to speeds of 300 to 600 m/s, which is sufficient to penetrate plant cell walls and membranes.

Another method for physical delivery of DNA to plants is sonication of target cells. Alternatively, liposome and spheroplast fusion can be used to introduce expression vectors into plants. Direct uptake of DNA into protoplasts using CaCl2 precipitation, polyvinyl alcohol or polyL-omithine has also been reported. Electroporation of protoplasts and whole cells and tissues has also been described. Following transformation of barley target tissues, expression of the above-described selectable marker genes allows for preferential selection of transformed cells, tissues and/or plants, using regeneration and selection methods.

The foregoing methods for transformation could be used for producing a transgenic variety. The transgenic variety could then be crossed with another (non-transformed or transformed) variety in order to produce a new transgenic variety. Alternatively, a genetic trait that has been engineered into a particular barley cultivar using the foregoing transformation techniques could be moved into another cultivar using traditional backcrossing techniques that are known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross, or the process of backcrossing, depending on the context.

Genetic Marker Profile Through SSR and First Generation Progeny

In addition to phenotypic observations, a plant can also be identified by its genotype. The genotype of a plant can be characterized through a genetic marker profile, which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as microsatellites, and Single Nucleotide Polymorphisms (SNPs).

Particular markers used for these purposes are not limited to any particular set of markers but are envisioned to include any type of marker and marker profile that provides a means of distinguishing varieties. One method of comparison is to use only homozygous loci for AS-Wolf.

In addition to being used for identification of barley cultivar AS-Wolf and plant parts and plant cells of cultivar AS-Wolf, the genetic profile may be used to identify a barley plant produced through the use of AS-Wolf or to verify a pedigree for progeny plants produced through the use of AS-Wolf. The genetic marker profile can also be useful in breeding and developing backcross conversions.

Means of performing genetic marker profiles using SSR polymorphisms are known. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. PCR detection uses two oligonucleotide primers flanking the polymorphic segment of repetitive DNA. Repeated cycles of heat denaturation of the DNA, followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties, all SSR profiles may be performed in the same lab.

The SSR profile of barley plant AS-Wolf can be used to identify plants comprising AS-Wolf as a parent, since such plants will comprise the same homozygous alleles as AS-Wolf. Because the barley variety is essentially homozygous at all relevant loci, most loci should have only one type of allele present. In contrast, a genetic marker profile of an F1 progeny should be the sum of those parents, e.g., if one parent was homozygous for allele x at a particular locus, and the other parent homozygous for allele y at that locus, then the F1 progeny will be xy (heterozygous) at that locus. Subsequent generations of progeny produced by selection and breeding are expected to be of genotype x (homozygous), y (homozygous), or xy (heterozygous) for that locus position. When the F1 plant is selfed or sibbed for successive filial generations, the locus should be either x or y for that position.

In addition, plants and plant parts substantially benefiting from the use of AS-Wolf in their development, such as AS-Wolf comprising a backcross conversion, transgene, or genetic sterility factor, may be identified by having a molecular marker profile with a high percent identity to AS-Wolf. In an embodiment, such a percent identity might be 95%, 96%, 97%, 98%, 99%, 99.5%, or 99.9% identical to AS-Wolf.

The SSR profile of AS-Wolf also can be used to identify essentially derived varieties and other progeny varieties developed from the use of AS-Wolf, as well as cells and other plant parts thereof. Progeny plants and plant parts produced using AS-Wolf may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from AS-Wolf, as measured by either percent identity or percent similarity. Such progeny may be further characterized as being within a pedigree distance of AS-Wolf, such as within 1, 2, 3, 4, 5, or more cross pollinations to a barley plant other than AS-Wolf or a plant that has AS-Wolf as a progenitor. Unique molecular profiles may be identified with other molecular tools such as SNPs and RFLPs.

While determining the SSR genetic marker profile of a plant as described above, several unique SSR profiles may also be identified that did not appear in either parent plant. Such unique SSR profiles may arise during the breeding process from recombination or mutation. A combination of several unique alleles provides a means of identifying a plant variety, an F1 progeny produced from such variety, and further progeny produced from such variety.

Gene Conversion

When the term "barley plant" is used in the context of the present innovation, this term also includes any gene conversions of that variety. Backcrossing methods can be used with the present innovation to improve or introduce a characteristic into the variety. For example, a variety may be backcrossed 1, 2, 3, 4, 5, 6, 7, 8, 9, or more times to the recurrent parent. The parental barley plant that contributes the gene for the desired characteristic is termed the "nonrecurrent" or "donor" parent. This terminology refers to the fact that the nonrecurrent parent is used one time in the backcross protocol and therefore does not recur. The parental barley plant to which the gene or genes from the nonrecurrent parent are transferred is known as the recurrent parent, as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a barley plant is obtained wherein essentially all of the desired morphological and physiological characteristics of the recurrent parent are recovered in the converted plant, in addition to the single transferred gene from the nonrecurrent parent.

The selection of a suitable recurrent parent contributes to a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add commercially desirable, agronomically important traits to the plant. The exact backcrossing protocol will depend on the characteristic or trait being altered. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many single gene traits have been identified that are not regularly selected for in the development of a new variety, but that can be improved by backcrossing techniques. Single gene traits may or may not be transgenic. Examples of these traits include, but are not limited to, male sterility, waxy starch, herbicide tolerance or resistance, resistance for bacterial, fungal, or viral disease, insect resistance or tolerance, male fertility, enhanced nutritional quality, industrial usage, yield stability, and yield enhancement. These genes are generally inherited through the nucleus.

Mutation Breeding

Mutation breeding is another method of introducing new traits into barley cultivar AS-Wolf. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation, such as X-rays, Gamma rays (e.g. cobalt 60 or cesium 137), neutrons (product of nuclear fission by uranium 235 in an atomic reactor), Beta radiation (emitted from radioisotopes such as phosphorus 32 or carbon 14), or ultraviolet radiation (for example, from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Once a desired trait is observed through mutagenesis the trait may then be incorporated into existing germplasm by traditional breeding techniques. In addition, mutations created in other barley plants may be used to produce a backcross conversion of barley cultivar AS-Wolf that comprises such mutations.

Further embodiments include the treatment of AS-Wolf with a mutagen and the plant produced by mutagenesis of AS-Wolf.

EXAMPLES

In one aspect of the present disclosure, barley cultivar AS-Wolf was tested for agronomic performance. Comparisons between AS-Wolf and other barley varieties are presented in Tables 3 through 5. Those skilled in the art will recognize that these are values that may vary due to environmental conditions and that other values that are substantially equivalent are within the scope of the present disclosure.

Specifically, pounds of barley produced per acre were examined for AS-Wolf in comparison to 13 to 16 other barley varieties/lines. Additional agronomic performance metrics were tested between the presently-disclosed AS-Wolf and the varieties/lines mentioned. In each table, Column 1 lists the variety/lines that were compared. Column 2 lists the number of pounds produced per acre. In Tables 3 and 4, Column 3 lists the Heading Date in days after planting and Column 4 lists the Height in centimeters (cm). In Table 3, Column 5 lists the Beta-glucan (%) on an as-is moisture basis. In Table 5, Column 3 lists the Test Weight in pounds per bushel. Table 3 shows information collected in Casselton, ND in 2018 and Table 4 shows similar information in Casselton, ND in 2019. Table 5 shows information collected in Central California in 2019. In each Table, statistics are provided to show the trial mean, the coefficient of variation (CV) for the trial and the Least Significant Difference (LSD) between lines at the 0.05 level of probability.

TABLE 3

Evaluation of Tamalpais derived F5 in 2018 Casselton, ND (2 replications).

| Genotype | Yield -lbs/a- | Heading Date -days after planting- | Height -cm- | Beta-Glucan - % as-is - |
|---|---|---|---|---|
| Rasmusson | 4591.0 | 46 | 82.6 | 4.41 |
| Genesis | 4534.1 | 47 | 83.8 | 4.61 |
| W039-1 | 4516.8 | 43 | 61.0 | 8.33 |
| AS-Wolf (Y039-1) | 4420.4 | 48 | 53.3 | 8.16 |
| Y039-5 | 4263.8 | 46 | 63.5 | 7.79 |
| W007-1 | 4096.5 | 43 | 66.0 | 7.07 |
| Y039-2 | 4005.4 | 45 | 62.2 | 8.90 |
| Y008-1 | 3895.2 | 46 | 59.7 | 7.68 |
| Y007-1 | 3883.7 | 46 | 69.9 | 8.14 |
| W007-2 | 3618.6 | 44 | 53.3 | 8.23 |
| Y070-1 | 3589.2 | 50 | 57.2 | 8.50 |
| W010-1 | 3543.8 | 43 | 58.4 | 8.14 |
| AKF-Ace | 3462.1 | 51 | 78.7 | 6.48 |
| Y010-1 | 3337.5 | 49 | 57.2 | 7.20 |
| AS-007 (Y007-3) | 3270.1 | 50 | 58.4 | 7.79 |
| Y039-4 | 3194.4 | 48 | 64.8 | 8.01 |
| Tamalpais | 2702.4 | 47 | 63.5 | 7.20 |
| LSD 0.05 | 393.8 | 1.6 | 7.4 | — |
| Plot Mean | 3779.8 | 47.0 | 63.9 | 7.45 |
| CV | 5.0 | 1.7 | 5.5 | — |

TABLE 4

Evaluation of Breeding lines grown in
a 3-rep trial in 2019 Casselton, ND.

| Genotype | Yield -lbs/a- | Heading -days after planting- | Height -cm- |
|---|---|---|---|
| Genesis | 2830.8 | 54.5 | 81.3 |
| Y007-1 | 2538.9 | 48.0 | 64.8 |
| Rasmusson | 2525.5 | 51.5 | 68.6 |
| AKF-Ace | 2523.6 | 55.0 | 72.4 |
| AS-007 (Y007-3) | 2357.8 | 50.0 | 54.6 |
| Y039-5 | 2350.1 | 50.0 | 59.7 |
| W007-1 | 2319.8 | 48.5 | 62.2 |
| Y010-1 | 2284.9 | 49.5 | 61.0 |
| W007-2 | 2236.4 | 53.0 | 50.8 |
| W039-1 | 2154.6 | 49.0 | 62.2 |
| Y039-2 | 2108.0 | 49.0 | 62.2 |
| Y039-4 | 2052.4 | 49.5 | 61.0 |
| Y008-1 | 2047.0 | 49.0 | 61.0 |
| AS-Wolf (Y039-1) | 1955.0 | 50.5 | 64.8 |
| Y070-1 | 1935.5 | 51.5 | 52.1 |
| W010-1 | 1845.1 | 50.0 | 58.4 |
| Tamalpais | 1689.2 | 51.0 | 55.9 |
| LSD 0.05 | 595 | 2.0 | 7.8 |
| Plot Mean | 2116.6 | 50.8 | 61.4 |
| CV | 14.1 | 2.0 | 6.4 |

TABLE 5

Evaluation of F6 lines in a 4-rep trial in Central California in 2019.

| Genotype | Yield -lbs/a- | Test Weight -lbs/bu- |
|---|---|---|
| Y007-1 | 3124.8 | 64.6 |
| Y039-4 | 2840.6 | 63.7 |
| Y039-5 | 2679.6 | 63.6 |
| AS-Wolf (Y039-1) | 2328.7 | 64.1 |
| Y010-1 | 2182.3 | 64.2 |
| W039-1 | 2176.5 | 64.0 |
| AS-007 (Y007-3) | 2105.4 | 64.5 |
| W007-2 | 2038.7 | 63.7 |
| Y070-1 | 1938.7 | 62.5 |
| Tamalpais | 1908.2 | 61.9 |
| W010-1 | 1873.4 | 63.0 |
| Y039-2 | 1680.6 | 63.4 |
| Y008-1 | 1667.5 | 62.7 |
| W007-1 | 1567.5 | 63.9 |
| LSD 0.05 | 288.6 | 0.5 |
| Plot Mean | 2133.0 | 63.5 |
| CV | 9.8 | 0.6 |

Table 6 compares AS-Wolf grown in a Breeder Seed increase field with 2 additional varieties/lines grown in the same location in the Central Valley of California in 2020 and in replicated trials in 2021. Column 1 lists the variety/lines that were compared, specifically AS-007 and Tamalpais. Column 2 lists the Average Heading Date in days after planting and Column 3 lists the Average Height in centimeters (cm).

TABLE 6

Comparisons in 2020-2021 Central Valley of California (n = 5).

| Variety | Average Heading -days after planting- | Average Height -cm- |
|---|---|---|
| AS-007 | 81.5 | 62.1 |
| AS-Wolf | 80.0 | 68.6 |
| Tamalpais | 83.4 | 71.2 |

As can be seen from the results shown in Tables 3-6, AS-Wolf exhibits increased grain yields in terms of pounds produced per acre as compared to Tamalpais, a variety well adapted to the Central Valley of California. Additionally, AS-Wolf exhibits decreased heading time and height in California as compared to Tamalpais but slightly taller than AS-007. This results in a barley plant that produces more barley per acre having waxy starch and higher Beta-glucan % which is desirable to some food production manufacturers. The variations in agronomic performance can allow growers to select varieties with optimal traits for their growing environments.

Deposit Information

A deposit of the barley cultivar AS-Wolf disclosed above and recited in the appended claims has been made with the American Type Culture Collection (ATCC), 10801 University Boulevard, Manassas, Va. 20110. The date of deposit was Jan. 27, 2022 and the accession number for those deposited seeds of barley cultivar AS-Wolf is ATCC Accession No. PTA-127269. All restrictions on this deposit have been removed, and the deposit is intended to meet all of the requirements of 37 C.F.R. §§ 1.801-1.809. The deposit will be maintained in the depository for a period of thirty years, or five years after the last request, or for the enforceable life of the patent, whichever is longer, and will be replaced if necessary, during that period.

All the compositions and methods disclosed and claimed herein can be made and executed without undue experimentation in light of the present disclosure. While the compositions and methods of this disclosure have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the innovation as defined by the appended claims.

Although the application describes embodiments having specific structural features and/or methodological acts, it is to be understood that the claims are not necessarily limited to the specific features or acts described. Rather, the specific features and acts are merely illustrative of some embodiments that fall within the scope of the claims of the application.

What is claimed is:

1. A plant, plant part, seed, or plant cell of barley variety AS-Wolf, representative seed of said variety having been deposited under ATCC accession number PTA-127269.

2. A barley seed produced from (i) selfing the plant or plant part of claim 1 or (ii) crossing of the plant or plant part of claim 1 with a different barley plant or plant part.

3. A barley plant or plant part produced by growing the barley seed of claim 2.

4. The barley seed of claim 2, wherein the seed is an F1 hybrid barley seed.

5. A method for producing a progeny seed, the method comprising crossing the barley plant of claim 3, to a plant of barley variety AS-Wolf, representative seed of said variety having been deposited under ATCC accession number PTA-127269 and producing a progeny seed.

6. The method of claim 5, wherein the method further comprises crossing a plant grown from the progeny seed to a plant of barley variety AS-Wolf and producing a backcrossed seed.

7. The backcrossed seed produced by the method of claim 6.

8. A method for producing a second barley plant, the method comprising applying plant breeding techniques to the barley plant or plant part of claim 3, wherein application of said techniques results in the production of a second barley plant.

9. A method for producing a second barley plant, the method comprising doubling haploid seed generated from a cross of the barley plant or plant part of claim 3 with a different barley plant.

10. A method for producing nucleic acids, the method comprising isolating nucleic acids from the plant, plant part, seed, or plant cell of claim 1.

11. A method of producing a commodity plant product from barley variety AS-Wolf comprising obtaining the plant, plant part, seed, or plant cell of claim 1 and producing the product therefrom.

12. The method of claim 11, wherein the commodity plant product is grain, flour, bran, baked goods, cereals, pasta, beverages, malts, extractions or medicines.

13. A barley plant produced by introducing a locus conversion into barley variety AS-Wolf, wherein the locus conversion was introduced by backcrossing or genetic transformation into barley variety AS-Wolf and wherein a sample of barley variety AS-Wolf has been deposited under ATCC Accession No. PTA-127269.

14. The barley plant of claim 13, wherein the locus conversion comprises a transgene.

15. The plant, plant part, seed, or plant cell of claim 13, wherein the locus conversion confers a trait selected from the group consisting of male sterility, abiotic stress tolerance, altered phosphate content, altered protein, altered antioxidants, altered fatty acids, altered essential amino acids, altered carbohydrates, tolerance/resistance to an herbicide, insect or disease, wherein the altered trait is compared with a plant of barley variety AS-Wolf not comprising the locus conversion.

16. A tissue culture produced from the plant, plant part, seed, or plant cell of claim 13.

17. A barley seed produced by crossing the plant of claim 13 with a different barley plant.

18. A barley plant produced by growing the barley seed of claim 16.

19. A method for producing a second barley plant comprising applying plant breeding techniques to the barley plant of claim 17, wherein application of said techniques results in the production of a second barley plant.

* * * * *